United States Patent [19]
Ouki et al.

[11] Patent Number: 5,647,897
[45] Date of Patent: Jul. 15, 1997

[54] INK COMPOSITION FOR INK JET RECORDING

[75] Inventors: Yasuhiro Ouki; Miharu Kanaya; Hiroko Hayashi; Kiyohiko Takemoto; Masaaki Itano, all of Suwa, Japan

[73] Assignee: Seiko Epson Corporation, Tokyo-to, Japan

[21] Appl. No.: 550,686

[22] Filed: Oct. 31, 1995

[30] Foreign Application Priority Data

| | | | |
|---|---|---|---|
| Nov. 7, 1994 | [JP] | Japan | 6-272028 |
| Jan. 18, 1995 | [JP] | Japan | 7-005857 |
| May 23, 1995 | [JP] | Japan | 7-123971 |

[51] Int. Cl.$^6$ ............................................. C09D 11/02
[52] U.S. Cl. ........................... 106/31.49; 106/31.52; 106/31.58; 534/833; 534/836; 534/837
[58] Field of Search ..................... 106/22 K, 22 H, 106/22 R; 534/833, 836, 837

[56] References Cited

U.S. PATENT DOCUMENTS

| | | | |
|---|---|---|---|
| 4,620,876 | 11/1986 | Fujii et al. | 106/22 K |
| 4,963,189 | 10/1990 | Hindagolla | 106/22 |
| 5,203,912 | 4/1993 | Greenwood et al. | 106/22 |
| 5,421,871 | 6/1995 | Onishi et al. | 106/22 K |

FOREIGN PATENT DOCUMENTS

| | | |
|---|---|---|
| 0494523 | 7/1992 | European Pat. Off. . |
| 0597672 | 5/1994 | European Pat. Off. . |
| 59093766 | 5/1984 | Japan . |
| 236279 | 2/1990 | Japan . |
| 391577 | 4/1991 | Japan . |

OTHER PUBLICATIONS

Patent Abstracts of Japan, English Translation of JP 59093766, May 1984.
Derwent Abstract English Translation of JP 3–91577, Apr. 1991.
Patent Abstracts of Japan, English Translation of 02036279A, Feb. 1990.
Derwent Abstract, English Translation of JP 4–226175, Aug. 1992.
Derwent Abstract, English Translation of JP 4233975, Aug. 1992.

*Primary Examiner*—Helene Klemanski
*Attorney, Agent, or Firm*—Ladas & Parry

[57] ABSTRACT

An ink composition for ink jet recording is provided which can satisfy property requirements of quality of print, drying property of print, clogging resistance, water resistance, storage stability, and nonattacking on members constituting an ink passage, such as a printing head. The ink composition for ink jet recording comprises a dye represented by the following formula (I), glycerin, pyrrolidone, a monohydric lower alcohol, a tri(hydroxyalkyl)amine, and water:

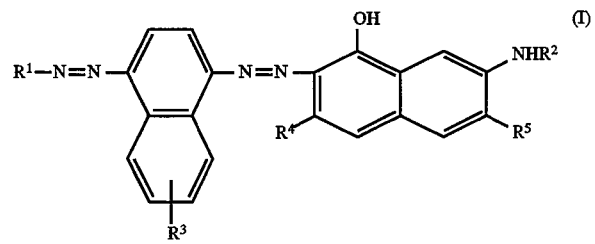

wherein $R^1$ represents phenyl or naphthyl substituted by a group selected from hydroxyl, —$NH_2$, —$SO_3M$ and —COOM, $R^2$ represents carboxyalkyl, alkoxyalkyl, phenyl, or alkanoyl, $R^3$, $R^4$, and $R^5$ represent hydrogen or —$SO_3M$.

19 Claims, No Drawings

INK COMPOSITION FOR INK JET RECORDING

BACKGROUND OF THE INVENTION

1. Technical Field

The present invention relates to an ink composition having excellent reproduction of black and an ink jet recording method using the same.

2. Background Art

An ink composition for ink jet recording is required to have the following properties.

(1) Good print and image quality can be realized on various recording media, especially plain paper.

(2) The drying rate of the ink after printing is high enough to cause no smear even when the print is rubbed immediately after printing.

(3) Ink droplets can be stably ejected through nozzles of a printing head nozzle without causing unfavorable phenomena such as clogging, dropout, and without ejecting ink droplets with trajectories non-perpendicular to the printing head.

(4) The resultant print has water resistance high enough to cause, upon contact with water, neither defacement of the print nor washing away of the print.

(5) The storage stability of the ink composition is enough not to cause any change in properties even when the ink composition is stored for a long period of time.

(6) The ink composition does not attack printer members which come into contact with the ink composition.

In particular, a black ink composition is important for ink jet recording in both monochrome printing and full-color printing and, thus, should satisfy the above property requirements.

Various black ink compositions have been proposed with a view to satisfying the above property requirements.

For example, C.I. Food Black 2 (Japanese Patent Laid-Open Publication No. 93766/1984) and dyes having structures similar thereto (Japanese Patent Laid-Open Publication No. 91577/1991) have been used widely as a dye for a black ink in the art. Further, an attempt was made to use a particular ink composition to improve properties such as lightfastness (Japanese Patent Laid-Open Publication No. 36279/1990). Furthermore, several proposals have been made to improve the water resistance of the print (for example, Japanese Patent Laid-Open Publication Nos. 91577/1991, 226175/1992, and 233975/1992).

Furthermore, U.S. Patent Nos. 4,963,189 and 5,203,912 describe dyes. (Some of the dyes are covered by the formula (I) described below.) The dyes described in the U.S. patents can be easily dissolved in basic water but are insoluble in neutral water. These patents describe that, by taking advantage of this property, the ink composition containing the dyes can improve the water resistance of the print.

The conventional ink compositions, however, have room for improvement, and a need still exists for an ink composition capable of satisfying the property requirements (1) to (6).

SUMMARY OF THE INVENTION

The present inventors have now found that an ink composition having excellent properties can be provided by combining a dye having a specific structure with specific components.

Accordingly, an object of the present invention is to provide an ink composition having a good balance of various properties required of an ink composition, especially the properties (1) to (6).

More specifically, an object of the present invention is to provide an ink composition, for ink jet recording, which can satisfy property requirements such as quality of print, drying property of print, clogging resistance, water resistance, storage stability, and nonattacking on members constituting ink passages, such as a printing head.

The ink composition of the present invention comprises a dye represented by the following formula (I), glycerin, pyrrolidone, a monohydric lower alcohol, a tri(hydroxyalkyl)amine, and water:

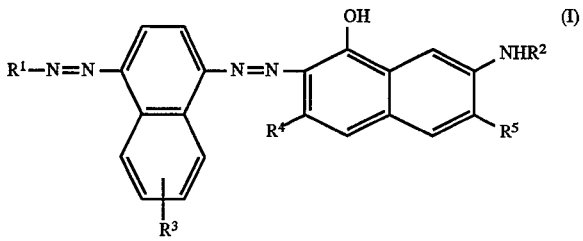

wherein $R^1$ represents phenyl or naphthyl, said phenyl and naphthyl may being substituted by a group selected from the group consisting of hydroxyl, $—NH_2$, $—SO_3M$ and $—COOM$ wherein M represents a hydrogen atom or a cation derived from an alkali metal, ammonia, or an amine, $R^2$ represents carboxyalkyl in which the carboxyl group may form a salt with an alkali metal or ammonia; unsubstituted or substituted alkoxyalkyl; unsubstituted or substituted phenyl; or alkanoyl, and $R^3$, $R^4$, and $R^5$, which may be the same or different, independently represent hydrogen or $—SO_3M$ wherein M is as defined above, except for the compound in which $R^1$ represents phenyl substituted by $—SO_3M$ When all of $R^3$, $R^4$, and $R^5$ represent $—SO_3M$.

DETAILED DESCRIPTION OF THE INVENTION

The essential components of the ink composition according to the present invention are a dye represented by the formula (I), glycerin, pyrrolidone, a monohydric lower alcohol, a tri(hydroxyalkyl)amine, and water.

In the formula (I), the phenyl or naphthyl group as $R^1$ may be unsubstituted or substituted. When $R^1$ represents a substituted phenyl group, it is preferably a monosubstituted phenyl group (substituted preferably at the 3-position or 4-position) or a disubstituted phenyl group (substituted preferably at the 2,4-positions or 3,5-positions). Preferred substituents include hydroxyl, $—NH_2$, sulfonic, and carboxy groups. The sulfonic and carboxy groups may be either free acid form or salt form. Preferred salts include alkali metal, ammonia, and amine salts, preferably tri(hydroxy $C_{1-6}$ alkyl) amine.

The naphthyl group as $R^1$ may be 1- or 2-naphthyl group. Further, it may be unsubstituted or substituted. When $R^1$ represents a substituted naphthyl group, preferred substituents include the same substituents described as those of the phenyl group.

In the formula (I), the carboxyalkyl group as $R^2$ is preferably a carboxy $C_{1-6}$ alkyl group, still preferably a carboxy $C_{1-4}$ alkyl group. Preferably, the carboxy group may form a salt with an alkali metal or ammonia. The alkoxyalkyl group as $R^2$ is preferably a $C_{1-6}$ alkoxy-$C_{1-6}$ alkyl group, still preferably a $C_{1-4}$ alkoxy-$C_{1-4}$ alkyl. One or more hydrogen atoms in the alkoxyalkyl group may be substituted, preferably, by hydroxyl and —$NH_2$. The phenyl group as $R^2$ may be substituted, preferably, by hydroxyl and —$NH_2$. Further, the alkanoyl group as $R^2$ is preferably a $C_{1-6}$ alkanoyl, still preferably $C_{1-4}$ alkanoyl.

In the formula (I), $R^3$, $R^4$, and $R^5$ may be the same or different and independently represent a hydrogen atom or a sulfonic group. The sulfonic group may be either free acid from or salt form. Preferred salts include alkali metal, ammonia, and amine salts, preferably tri(hydroxy $C_{1-6}$ alkyl) amine.

Compounds represented by the formula (I) wherein $R^1$ represents a phenyl group substituted by —$SO_3M$ and, at the same time, all of $R^3$, $R^4$, and $R^5$ represent —$SO_3M$ cannot be used in the ink composition of the present invention. According to experiments conducted by the present inventors, the ink compositions using such compounds were unsatisfactory in various necessary properties.

Preferred specific examples of compounds represented by the formula (I) are as given in the following tables.

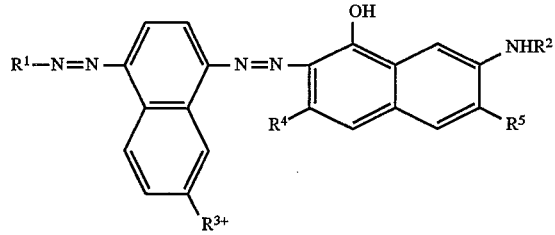

| Compound No. | $R^1$ | $R^2$ | $R^{3*}$ | $R^4$ | $R^5$ |
|---|---|---|---|---|---|
| 1 | NaO₃S—⟨phenyl⟩— | H | H | —$SO_3Na$ | —$SO_3Na$ |
| 2 | COOLi—⟨phenyl⟩— | —$CH_2COOLi$ | —$SO_3Li$ | —$SO_3Li$ | H |
| 3 | ⟨phenyl⟩— | —$COCH_3$ | —$SO_3Na$ | —$SO_3Na$ | —$SO_3Na$ |
| 4 | COONH₄—⟨phenyl⟩— | —$CH_2CHCH_2OC_4H_9$ \| OH | —$SO_3NH_4$ | —$SO_3NH_4$ | H |
| 5 | COONH₄—⟨phenyl⟩— | H | —$SO_3NH_4$ | —$SO_3NH_4$ | H |
| 6 | NaOOC—⟨phenyl⟩— | —$CH_2CHCH_2OC_2H_5$ \| OH | H | —$SO_3Na$ | H |
| 7 | COONH₄—⟨phenyl⟩— | H | H | H | —$SO_3NH_4$ |
| 8 | HO—⟨phenyl⟩— | H | —$SO_3Na$ | —$SO_3Na$ | H |

-continued
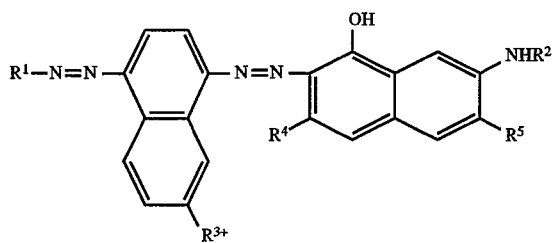
| Compound No. | R¹ | R² | R³* | R⁴ | R⁵ |
|---|---|---|---|---|---|
| 9 | H₄NOOC—C₆H₄— | H | —SO₃NH₄ | —SO₃NH₄ | H |
| 10 | 3-NH₂-4-CH₃-C₆H₃(SO₃Na)— | —CH₂COONa | —SO₃Na | —SO₃Na | H |
| 11 | 3-OH-4-CH₃-C₆H₃(COONH₄)— | —CH₂CH₂COONH₄ | H | —SO₃NH₄ | H |
| 12 | 3-SO₃Li-naphthyl— | H | —SO₃Li | —SO₃Li | H |
| 13 | 1-HO-6-NaO₃S-naphthyl— | H | —SO₃Na | —SO₃Na | —SO₃Na |
| 14 | 5-NaO₃S-7-NH₂-naphthyl— | 4-OH-C₆H₄— | H | —SO₃Na | H |
| 15 | 5-HO-7-NaOOC-naphthyl— | —CH₂COONa | H | —SO₃Na | —SO₃Na |

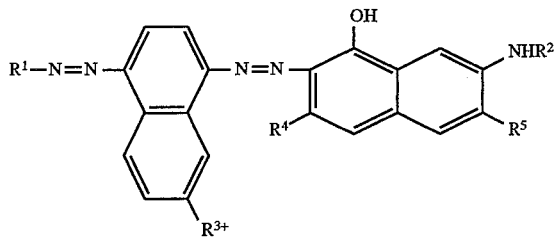

| Compound No. | R¹ | R² | R³* | R⁴ | R⁵ |
|---|---|---|---|---|---|
| 16 | 3,5-di(COOLi)phenyl | $-CH_2CH_2COOLi$ | $-SO_3Li$ | $-SO_3Li$ | H |
| 17 | 2-naphthyl | H | $-SO_3Li$ | $-SO_3Li$ | H |
| 18 | 1-OH-5-$SO_3NH_4$-naphth-2-yl | $-COCH_3$ | H | $-SO_3NH_4$ | $-SO_3NH_4$ |
| 19 | 1-$NH_2$-naphth-2-yl | H | $-SO_3Na$ | H | $-SO_3Na$ |
| 20 | 3-($COONH_4$)phenyl | H | $-SO_3NH_4$ | $-SO_3NH_4$ | H |
| 21 | 3,5-di(COONa)phenyl | H | H | $-SO_3Na$ | $-SO_3Na$ |
| 22 | 3,5-di($COONH_4$)phenyl | H | $-SO_3NH_4$ | $-SO_3NH_4$ | H |
| 23 | 3,5-di($COONH(C_2H_5OH)_3$)phenyl | $-COCH_3$ | $-SO_3NH(C_2H_5OH)_3$ | $-SO_3NH(C_2H_5OH)_3$ | H |

The dye represented by the formula (I) may be prepared by known methods or methods similar thereto. For example, the dye represented by the formula (I) may be prepared by methods described in Japanese Patent Laid-Open Publication No. 140270/1990 and Color index, Third Edition, The Society of Dyers and Colourists.

The dye represented by the formula (I) is soluble in water under basic conditions but insoluble in water under neutral conditions. Therefore, preferably, the ink composition of the present invention has a pH value on the basic side. However, excessively high pH value should be avoided because the dye is likely to be decomposed. According to a preferred embodiment of the present invention, the pH value of the ink composition is preferably in the range of from about 8.5 to 11, still preferably about 8.5 to 10. The pH value of the ink composition is regulated by the formulation of the ink described below, especially the amount of tri(hydroxyalkyl) amine added.

In the ink composition of the present invention, the content of the dye represented by the formula (I) is preferably in the range of from 1 to 5% by weight, still preferably 1 to 3% by weight.

In the ink composition of the present invention, the amount of glycerin added may be suitably determined in such an amount range that the ink composition has good various properties, especially good ejecting stability. It is preferably in the range of from about 1 to 10% by weight, still preferably 3 to 10% by weight.

In the ink composition of the present invention, the pyrrolidone is preferably 2-pyrrolidone or N-(2-hydroxyethyl)-2-pyrrolidone, still preferably 2-pyrrolidone. These pyrrolidones may be used alone or as a mixture of two or more. The amount of the pyrrolidone added may be suitably determined in such an amount range that the ink composition has good various properties, especially good printing stability and color reproduction. It is preferably in the range of from about 0.5 to 10% by weight, still preferably 2 to 6% by weight.

According to a preferred embodiment of the present invention, the weight ratio of glycerin to pyrrolidone in the ink composition is 3:1 to 2:3, preferably 3:1 to 1:1. When glycerin and pyrrolidone are contained in the above weight ratio, the adverse effect on materials constituting a printing head and an ink passage which come into contact with the ink composition, can be effectively prevented. Ink compositions containing pyrrolidone may cause phenomena, such as dissolution, swelling, cracking, or surface toughening of the materials constituting a printing head and an ink passage. The phenomena seem to derive from high dissolving power of pyrrolidone. Such phenomena is sometimes called an "attacking property" of the ink composition. When the weight ratio of glycerin to pyrrolidone falls within the above range, the attacking property of the ink composition can be effectively inhibited.

The tri(hydroxyalkyl)amine contained in the ink composition of the present invention is preferably tri(hydroxy $C_{1-6}$ alkyl)amine, still preferably tri(hydroxy $C_{1-4}$ alkyl)amine, most preferably triethanolamine. The amount of the tri (hydroxyalkyl)amine may be determined in such an amount range that the ink composition has good various properties, especially that the ink composition has a pH value on the basic side. It is preferably in the range of from about 0.1 to 2% by weight, still preferably about 0.3 to 1% by weight.

The monohydric lower alcohol contained in the ink composition of the present invention is preferably a monohydric alcohol having 1 to 6 carbon atoms, still preferably a monohydric alcohol having 1 to 4 carbon atoms. It is particularly preferably ethanol. The amount of the alcohol may be determined in such an amount range that the ink composition has good various properties, especially good drying property of the print. It is preferably in the range of from about 1 to 10% by weight, still preferably about 3 to 6% by weight.

According to a preferred embodiment of the present invention, the ink composition of the present invention further comprises at least one hydroxide of a metal selected from the group consisting of the group Ia and IIa metals of the periodic table. The addition of the metal hydroxide is advantageous in that various properties of the ink composition, especially resumption from clogging, can be further improved. Specific preferred examples of the metal oxide include LiOH, NaOH, and KOH. The amount of the metal oxide may be determined in such an amount range that the ink composition can have improved various properties, especially improved resumption from clogging. It is preferably in the range of from about 0.01 to 1% by weight, still preferably about 0.05 to 0.5% by weight.

According to a preferred embodiment of the present invention, the ink composition further comprises C.I. Direct Black 154 and/or C.I. Direct Black 168. C.I. Direct Black 154 and C.I. Direct Black 168 are dyes and, at the same time, have surface active properties. Therefore, they can improve the wettability of the head and ink passage formed of glass, nickel, stainless steel, a plastic, a photosensitive resin, or the like by the ink composition. This can eliminate the necessity of carrying out a treatment for rendering the printing head and the ink passage hydrophilic and can facilitate filling of the ink. Further, bubbles entrained in the printing head and the ink passages can be advantageously discharged without difficulty. The total amount of C.I. Direct Black 154 and/or C.I. Direct Black 168 is preferably in the range of from about 0.01 to 1% by weight, still preferably 0.1 to 0.5% by weight.

The ink composition may optionally contain various additives necessary for improving various properties of the ink composition. For example, viscosity modifiers, surface tension modifiers, specific resistance modifiers, fungicides, and chelating agents may be added to the ink composition.

The various properties of the ink composition according to the present invention may be properly determined so that the ink composition is suitable for ink jet recording. For example, the viscosity of the ink is preferably not more than 30 mPa.s at an operation temperature of 0° to 50° C. In order to realize higher response (for example, printing at about 2 pages/min for size A4), it is preferably in the range of from 1.2 to 20 mPa.s. The surface tension of the ink composition is preferably in the range of from about 35 to 60 mN/m at an operation temperature of 0° to 50° C.

After printing, the ink composition of the present invention on the recording medium may be heated and dried by suitable heating means (for example, hot air, a hot roll, a hot plate, or an infrared radiation) to fix the image.

EXAMPLES

The present invention will now be described in more detail with reference to the following examples, though it is not limited to these examples only.

Preparation of Ink Compositions

Ink compositions comprising components specified in Tables 1 and 2, i.e., ink compositions of Examples 1 to 9 and Comparative Examples 1 and 2 were prepared by the following method.

In the table, "Dye <compound No. of formula (I)>" is the compound number indicated in the above tables showing specific examples of compounds represented by the formula (I). Further, "%" is by weight.

After all components except for the monohydric alcohol were mixed together in the weight ratios specified in Table 1, the mixture was stirred at 80° C. for one hr. Thereafter, the mixture was self-cooled with stirring. When the temperature lowered to 40° C. or below, the monohydric alcohol was added to the mixture. The mixture was stirred for about 20 min and then filtered through a 0.8-μm membrane filter under reduced pressure. The pH value given in the following tables was measured with a pH meter manufactured by Horiba, Ltd.

(c) Ricopy 6200 (available from Ricoh Co., Ltd.), and (d) Canon Dry (available from Canon Sales Co., Inc.).

Evaluation Test 1: Quality of Print

Prints were observed with the naked eye and evaluated for sharpness of an image in terms of bleeding and density according to the following criteria.
⊚: Print free from bleeding with high density
○: Print with slight bleeding having no significant influence on the image and with high density
Δ: Print free from bleeding or with low density having no significant influence on the image

TABLE 1

| | Example | | | | | | | | |
|---|---|---|---|---|---|---|---|---|---|
| | 1 | 2 | 3 | 4 | 5 | 6 | 7 | 8 | 9 |
| Dye (compound No. of general formula (I) | <4>3 | <7>1 | <12>5 | <14>1 | <17>3 | <2>2 | <21>2 | <15>3 | <23>2 |
| Glycerin | 5 | 1 | 10 | 1.5 | 7 | 4 | 4 | 5 | 3 |
| 2-Pyrrolidone | 5 | 1.5 | 5 | 0.5 | 10 | 4 | 2 | 3 | 4 |
| Triethanolamine | 0.7 | 0.1 | 2 | 0.5 | 0.7 | 0.9 | 1.2 | 1 | 1.5 |
| Ethanol | 4 | 5 | 2.5 | 1 | 4 | 10 | 4 | 6 | 4 |
| C.I. Direct Black 168 | | | 0.01 | 0.5 | | 0.2 | | 0.2 | |
| C.I. Direct Black 154 | | 0.5 | | 0.5 | 0.3 | 0.2 | 0.3 | | |
| Proxel XL-2* | | | 0.3 | | | | | | 0.3 |
| LiOH | | | | | | | 0.01 | | |
| KOH | | | | | | | | 0.2 | |
| NaOH | | | | | | | | | 1 |
| Water | 82.3 | 90.9 | 75.19 | 95 | 75 | 78.7 | 88.49 | 81.6 | 84.2 |
| pH | 8.9 | 8.5 | 10.5 | 8.7 | 9.0 | 9.3 | 9.5 | 9.8 | 10.0 |

*: Fungicide manufactured by Zeneca

TABLE 2

| | Comparative Example | | | | | | | |
|---|---|---|---|---|---|---|---|---|
| | 1 | 2 | 3 | 4 | 5 | 6 | 7 | 8 |
| Dye (compound No. of general formula (I) | <4>0.5 | <7>6 | <12>4 | <14>2 | <17>3 | <2>5 | <15>3 | <23>2 |
| Glycerin | 2 | 6 | 12 | 0.5 | 1.2 | | 5 | 3 |
| 2-Pyrrolidone | 4 | 4 | 3 | 15 | 0.4 | 8 | 3 | 4 |
| Triethanolamine | 0.7 | 2.5 | 1.5 | 0.05 | 1 | 0.8 | | 1.5 |
| Ethanol | 4 | 6 | 4 | 3 | 0.5 | 12 | 6 | 4 |
| C.I. Direct Black 168 | | 0.5 | 0.3 | | | | 0.2 | |
| C.I. Direct Black 154 | | 0.5 | | | | | | |
| Proxel XL-2* | | | | | | | | |
| LiOH | | | | | | | | |
| KOH | | | | | | | 0.2 | |
| NaOH | | | | | | | | 2 |
| Water | 88.8 | 74.5 | 75.2 | 79.45 | 91.9 | 74.2 | 82.6 | 83.2 |
| pH | 8.9 | 11.3 | 9.6 | 8.3 | 8.6 | 9.0 | 10.6 | 11.5 |

*: Fungicide manufactured by Zeneca

Evaluation Tests

Properties of the ink compositions of Examples and Comparative Examples thus prepared were evaluated as follows.

Ink jet printer MJ-500 (manufactured by Seiko Epson Corporation) was used in the evaluation tests. Ink cartridges, for a printer, filled with the inks of the examples of the present invention and comparative examples were used for the supply of the ink.

Evaluation involving a printing was carried out using as a recording medium (a) Xerox P (available from Fuji Xerox Co., Ltd.), (b) Xerox 4024 (available from Xerox U.S.A.), X: Print suffering from severe bleeding and with low density Evaluation Test 2: Drying Property of Print The print was allowed to stand for a predetermined period of time and then rubbed with an edge of the same type of paper as the recording medium to observe whether or not a trace of rubbing occurred.
⊚: No trace of rubbing occurred when rubbing was initiated 10 sec after printing.
○: No trace of rubbing occurred when rubbing was initiated 20 sec after printing.

Δ: No trace of rubbing occurred when rubbing was initiated 30 sec after printing.
X: A trace of rubbing occurred when rubbing was initiated 30 sec after printing.

Evaluation Test 3-1: Resumption from Clogging

After a printing head of a printer was filled with the ink, the head was allowed to stand under an environment of 40° C. and 20% (humidity) for one month and two months in such a state that the head was deviated from the position of a cap. Thereafter, printing was initiated to determine the number of times of cleaning required for return to normal printing.
⊚: 0 to twice
○: Three to four times
Δ: Five to six times
X: Not returned to normal printing even after cleaning six times

Evaluation Test 3-2: Printing Stability

Printing was continuously carried out using a self-check pattern provided in MJ-500 to determine the time of period for which printing could be stably carried out.
⊚: Not less than 24 hr
○: 10 to less than 24 hr
X: Less than 10 hr

Evaluation Test 3-3: Stability Against Intermittent Printing

Forty eight (48) ink droplets were ejected from the printing head for every 30 sec to determine the time of period for which printing could be stably carried out.
⊚: Not less than 10 hr
○: Not less than 1 hr to less than 10 hr
X: Less than 1 hr

Evaluation Test 4: Water Resistance

Water droplets were dropped on print areas of the print sample, and the print was then self-dried. The dried sample was evaluated as follows.
⊚: No change observed from the initial state
○: Letters are still legible although slight elution of dye occurred.
Δ: Letters are still legible although bleeding occurred.
X: Bleeding of letters occurred with letters being illegible.

Evaluation Test 5: Storage Stability

The ink composition was placed in a teflon bottle, sealed, and allowed to stand at −30=C. and 70° C. for one month. The change in properties and color tone between before and after standing and the occurrence of deposits/precipitates were evaluated as follows.
○: Neither change in properties and color tone nor occurrence of deposit/precipitate occurred.
X: Either change in properties and color tone or occurrence of deposit/precipitate or both of these unfavorable phenomena occurred.

Evaluation Test 6: Attacking Property

A printing head, a member constituting an ink passage, and a member constituting a cap of printer MJ-500 were immersed in an ink and, in this state, allowed to stand at 70° C. for one month. Thereafter, examination was carried out for unfavorable phenomena such as dissolution, swelling, cracking and surface roughening (attacking property of the ink composition) in the members and a change in properties of the ink and the occurrence of deposit/precipitate in the ink composition. The results were evaluated as follows.
○: None of attacking property, change in properties, and occurrence of deposit/precipitate were observed.
X: At least one of attacking property, change in properties, and occurrence of deposit/precipitate was observed.

The evaluation results were as given in the following tables.

TABLE 3

| | Example | | | | | | | | |
|---|---|---|---|---|---|---|---|---|---|
| | 1 | 2 | 3 | 4 | 5 | 6 | 7 | 8 | 9 |
| Quality of ink | | | | | | | | | |
| (a) | ⊚ | ○ | ⊚ | ○ | ⊚ | ⊚ | ⊚ | ⊚ | ⊚ |
| (b) | ⊚ | ○ | ⊚ | ○ | ⊚ | ⊚ | ⊚ | ⊚ | ⊚ |
| (c) | ⊚ | ○ | ⊚ | ○ | ⊚ | ⊚ | ⊚ | ⊚ | ⊚ |
| (d) | ⊚ | ○ | ⊚ | ○ | ○ | ○ | ⊚ | ⊚ | ⊚ |
| Drying property of ink | | | | | | | | | |
| (a) | ⊚ | ⊚ | ○ | ○ | ⊚ | ⊚ | ⊚ | ⊚ | ⊚ |
| (b) | ⊚ | ⊚ | ○ | ○ | ⊚ | ⊚ | ⊚ | ⊚ | ⊚ |
| (c) | ○ | ○ | ○ | ○ | ○ | ⊚ | ⊚ | ⊚ | ⊚ |
| (d) | ⊚ | ⊚ | ○ | ○ | ⊚ | ⊚ | ⊚ | ⊚ | ⊚ |
| Resumption from clogging | | | | | | | | | |
| one month | ⊚ | ○ | ⊚ | ○ | ⊚ | ⊚ | ⊚ | ⊚ | ⊚ |
| two months | ○ | ○ | ○ | ○ | ○ | ⊚ | ⊚ | ⊚ | ⊚ |
| Printing stability | ⊚ | ⊚ | ⊚ | ⊚ | ⊚ | ⊚ | ⊚ | ⊚ | ⊚ |
| Intermittent printing stability | ⊚ | ○ | ○ | ○ | ⊚ | ⊚ | ⊚ | ⊚ | ⊚ |
| Water resistance | | | | | | | | | |
| (a) | ○ | ○ | ○ | ○ | ○ | ○ | ⊚ | ⊚ | ⊚ |
| (b) | ⊚ | ○ | ○ | ○ | ○ | ○ | ⊚ | ⊚ | ⊚ |
| (c) | ○ | ○ | ○ | ○ | ○ | ○ | ⊚ | ⊚ | ⊚ |
| (d) | ⊚ | ○ | ○ | ○ | ○ | ○ | ⊚ | ⊚ | ⊚ |
| Storage stability | ○ | ○ | ○ | ○ | ○ | ○ | ○ | ○ | ○ |
| Long-term stability against contact with members constituting printer | ○ | ○ | ○ | ○ | ○ | ○ | ○ | ○ | ○ |

TABLE 4

| | Comparative Example | | | | | | | |
|---|---|---|---|---|---|---|---|---|
| | 1 | 2 | 3 | 4 | 5 | 6 | 7 | 8 |
| Quality of ink | | | | | | | | |
| (a) | Δ | ○ | ○ | ○ | ⊚ | ○ | ⊚ | ⊚ |
| (b) | Δ | ○ | ○ | ○ | ⊚ | X | ⊚ | ⊚ |
| (c) | Δ | Δ | ○ | ○ | ⊚ | ○ | ⊚ | ⊚ |
| (d) | Δ | ○ | X | X | ⊚ | X | ⊚ | ⊚ |
| Drying property of ink | | | | | | | | |
| (a) | ⊚ | ⊚ | ○ | ○ | ○ | ⊚ | ⊚ | ⊚ |
| (b) | ⊚ | ⊚ | ○ | ○ | Δ | ⊚ | ⊚ | ⊚ |
| (c) | ○ | ○ | Δ | Δ | Δ | ⊚ | ○ | ○ |
| (d) | ⊚ | ⊚ | ○ | ○ | ○ | ⊚ | ⊚ | ⊚ |
| Resumption from clogging | | | | | | | | |
| one month | ○ | ⊚ | ⊚ | Δ | ○ | X | X | —* |
| two months | ○ | ○ | ○ | Δ | ○ | X | X | —* |
| Printing stability | ⊚ | ⊚ | ○ | X | ○ | ○ | ⊚ | ⊚ |
| Intermittent printing stability | ⊚ | ⊚ | X | ⊚ | X | ⊚ | ⊚ | ⊚ |
| Water resistance | | | | | | | | |
| (a) | ○ | ○ | ○ | ○ | X | ○ | ○ | ○ |
| (b) | ⊚ | ○ | ○ | ○ | X | ○ | ○ | ○ |
| (c) | ○ | ○ | ○ | ○ | X | ○ | ○ | ○ |
| (d) | ⊚ | ○ | ○ | ⊚ | X | ⊚ | ○ | ○ |
| Storage stability | ○ | X | ○ | X | ○ | X | X | X |

TABLE 4-continued

| | Comparative Example | | | | | | | |
|---|---|---|---|---|---|---|---|---|
| | 1 | 2 | 3 | 4 | 5 | 6 | 7 | 8 |
| Long-term stability against contact with members constituting printer | x | o | o | x | o | x | o | o |

*: There are droprets with trajectories non-perpendicular to the printing head

We claim:

1. An ink composition for ink jet recording, comprising a dye represented by the following formula (1), glycerin, pyrrolidone, a monohydric lower alcohol, a tri(hydroxyalkyl)amine, and water:

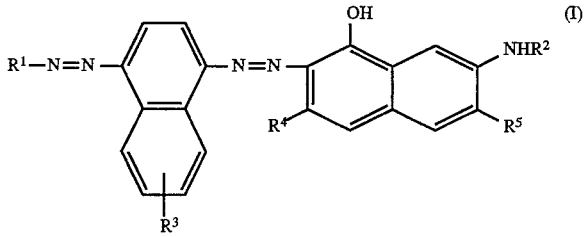

wherein $R^1$ represents phenyl or naphthyl, said phenyl and naphthyl groups may be substituted by a group selected from the group consisting of hydroxyl, $—NH_2$, $—SO_3M$ and $—COOM$ wherein M represents hydrogen or a cation derived from an alkali metal, ammonia, or an amine, $R^2$ represents carboxyalkyl in which the carboxyl group may form a salt with an alkali metal or ammonia; unsubstituted or substituted alkoxyalkyl, unsubstituted or substituted phenyl; or an alkanoyl, and $R^3$, $R^4$ and $R^5$, which may be the same or different, independently represent hydrogen or $—SO_3M$ wherein M is as defined above, except for the compound in which $R^1$ represents a phenyl group substituted by $—SO_3M$ when all of $R^3$, $R^4$ and $R^5$ represent $—SO_3M$; said ink composition further comprising at least one hydroxide of a metal selected from the group consisting of Group Ia and IIa metals of the Periodic Table of the Elements.

2. The ink composition according to claim 1, which has a pH value of 8.5 to 11.

3. The ink composition according to claim 1, which comprises 1 to 5% by weight of the dye represented by the formula (I), 1 to 10% by weight of glycerin, 0.5 to 10% by weight of pyrrolidone, 1 to 10% by weight of the monohydric lower alcohol, 0.1 to 2% by weight of the tri(hydroxyalkyl)amine, and 75 to 96.5% by weight of water.

4. The ink composition according to claim 1, wherein the pyrrolidone is 2-pyrrolidone.

5. The ink composition according to claim 1, wherein the weight ratio of glycerin to pyrrolidone is in the range of from 3:1 to 2:3.

6. The ink composition according to claim 1, wherein the tri(hydroxyalkyl)amine is an tri(hydroxy $C_{1-6}$ alkyl)amine.

7. The ink composition according to claim 6, wherein the tri(hydroxyalkyl)amine is triethanolamine.

8. The ink composition according to claim 1, wherein the monohydric lower alcohol is ethanol.

9. The ink composition according to claim 1, wherein the hydroxide is LiOH, NaOH, or KOH.

10. The ink composition according to claim 1, wherein the content of the hydroxide is 0.01 to 1% by weight.

11. The ink composition according to claim 1, which further comprises C.I. Direct Black 154, C.I. Direct Black 168 or mixtures thereof.

12. The ink composition according to claim 11, wherein the C.I. Direct Black 154, C.I. Direct Black 168 or mixtures thereof are contained in an amount of 0.01 to 1% by weight.

13. The ink composition according to claim 3 wherein the at least one hydroxide is present in the ink composition in an amount of about 0.01 to 1% by weight and the ink composition has a pH value of 8.5 to 11.

14. The ink composition according to claim 3 wherein the at least one hydroxide is present in the ink composition in an amount sufficient to reduce a tendency of the ink composition to clog the nozzle of a printing head.

15. The ink composition according to claim 14 wherein the ink composition further comprises C.I. Direct Black 143, C.I. Direct Black 168 or mixtures thereof in an amount of about 0.01 to 1% by weight.

16. In a method for ink jet recording comprising ejecting droplets of an ink composition through a nozzle of a printing head and onto a surface of a recording medium to form a print thereon, the improvement wherein the ink composition consists essentially of a dye represented by the following formula (I), glycerin, pyrrolidone, a monohydric lower alcohol, a tri(hydroxyalkyl)amine, and water:

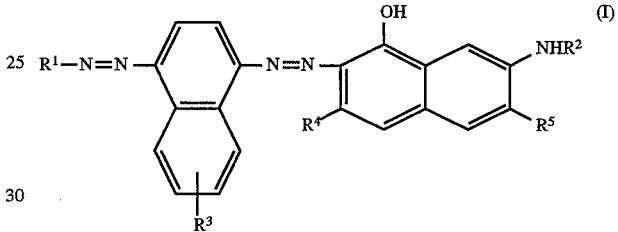

wherein $R^1$ represents phenyl or naphthyl, said phenyl and naphthyl groups may be substituted by a group selected from the group consisting of hydroxyl, $—NH_2$, $—SO_3M$ and $—COOM$ wherein M represents hydrogen or a cation derived from an alkali metal, ammonia, or an amine, $R^2$ represents carboxyalkyl in which the carboxyl group may form a salt with an alkali metal or ammonia; unsubstituted or substituted alkoxyalkyl; unsubstituted or substituted phenyl; or an alkanoyl, and $R^3$, $R^4$ and $R^5$, which may be the same or different, independently represent hydrogen or $—SO_3M$ wherein M is as defined above, except for the compound in which $R^1$ represents a phenyl group substituted by $—SO_3M$ when all of $R^3$, $R^4$ and $R^5$ represent $—SO_3M$; said ink composition further comprising at least one hydroxide of a metal selected from the group consisting of Group Ia and IIa metals of the Periodic Table of the Elements; said at least one hydroxide being present in the ink jet composition in an amount sufficient to reduce a tendency of the ink composition to clog the nozzle of a printing head or to improve a water resistance of the print.

17. A method according to claim 16 wherein the ink composition comprises 1 to 5% by weight of the dye represented by the formula (I), 1–10% by weight of glycerin, 0.5 to 10% by weight of pyrrolidone, 1 to 10% by weight of the monohydric lower alcohol, 0.1 to 2% by weight of the tri(hydroxyalkyl)amine, and 75 to 96.5% by weight of water.

18. A method according to claim 17 wherein the at lest one hydroxide is present in the ink composition in an amount of about 0.01 to 1% by weight.

19. A method according to claim 18 wherein the at least one hydroxide is LiOH, NaOH or KOH.

\* \* \* \* \*